United States Patent

Millot et al.

[11] Patent Number: 5,889,396
[45] Date of Patent: Mar. 30, 1999

[54] METHOD AND DEVICE FOR MEASURING THE QUANTITY OF AN ACTIVE PRINCIPLE CONTAINED IN A RESERVOIR

[75] Inventors: Philippe Millot; Anne Liotard, both of Dijon, France

[73] Assignee: Laboratoires d'Hygiene et de Dietetique (L.H.D.), Paris, France

[21] Appl. No.: 737,445
[22] PCT Filed: May 2, 1995
[86] PCT No.: PCT/FR95/00568
    § 371 Date: Oct. 31, 1996
    § 102(e) Date: Oct. 31, 1996
[87] PCT Pub. No.: WO95/30450
    PCT Pub. Date: Nov. 16, 1995

[30] Foreign Application Priority Data

May 6, 1994 [FR] France .................................. 94 05633

[51] Int. Cl.⁶ .................................................. G01N 27/04
[52] U.S. Cl. ........................ 324/71.1; 324/439; 324/693; 324/717
[58] Field of Search ..................... 324/439, 444, 324/459, 464, 693, 713, 717, 71.1

[56] References Cited

U.S. PATENT DOCUMENTS

| 3,531,252 | 9/1970 | Rivers | 324/439 |
| 3,794,910 | 2/1974 | Ninke et al. | 324/442 |
| 4,862,092 | 8/1989 | Juncosa | 324/450 |
| 5,047,723 | 9/1991 | Puumalainen | 324/464 |
| 5,049,808 | 9/1991 | Okahata | 324/71.1 |
| 5,289,132 | 2/1994 | Oksman et al. | 324/444 |

FOREIGN PATENT DOCUMENTS

| A-0277314 | 12/1987 | European Pat. Off. |
| A-0555510 | 2/1992 | European Pat. Off. |
| A-2562800 | 4/1984 | France |
| WO-A-90 03825 | 4/1990 | WIPO |

*Primary Examiner*—Glenn W. Brown
*Attorney, Agent, or Firm*—Stevens, Davis, Miller & Mosher, L.L.P.

[57] ABSTRACT

A solution of active principle, in ionized form, impregnates a layer (2) forming part of the reservoir (1). A measurement of the quantity of active principle contained in this layer is derived from a measurement of the conductivity of this layer. The measurement device comprises a) first (7) and second (10) electrodes placed on either side of and in electrical contact with at least a part of the layer (2) of the impregnated material of the reservoir, b) means (5) for passing the electric current of predetermined strength through the impregnated material and c) means (6) sensitive to the voltage (V) picked up between the electrodes (7, 10) in order to calculate the quantity of active principle contained in the reservoir.

14 Claims, 1 Drawing Sheet

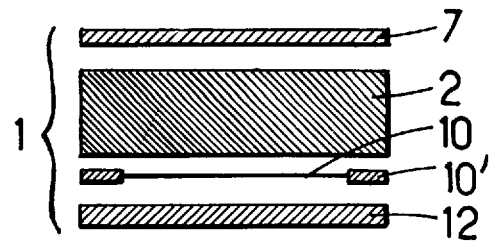
FIG.:1
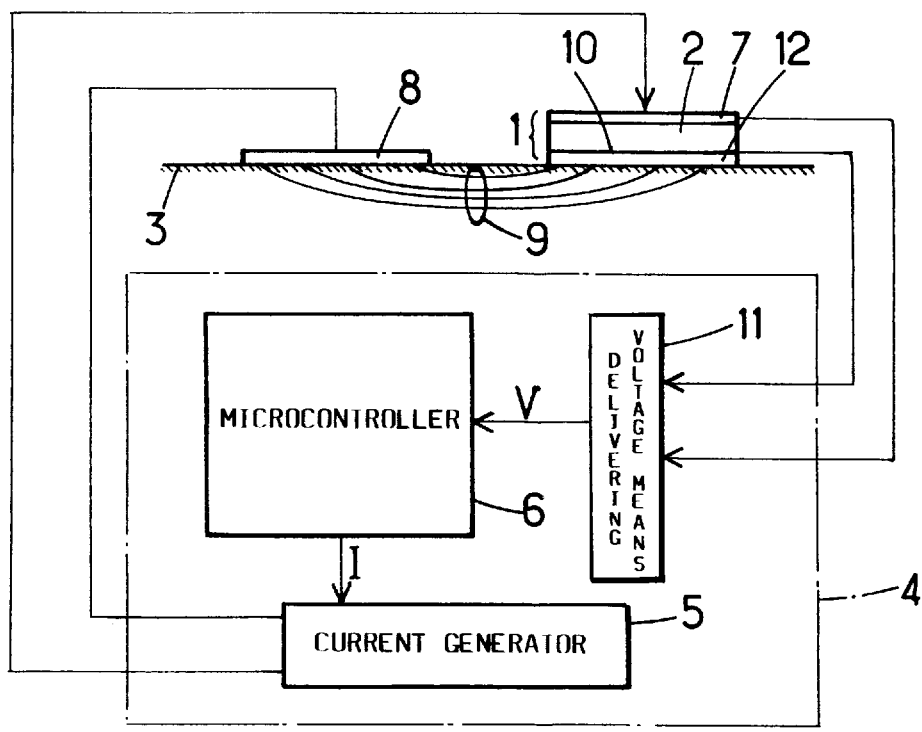
FIG.:2
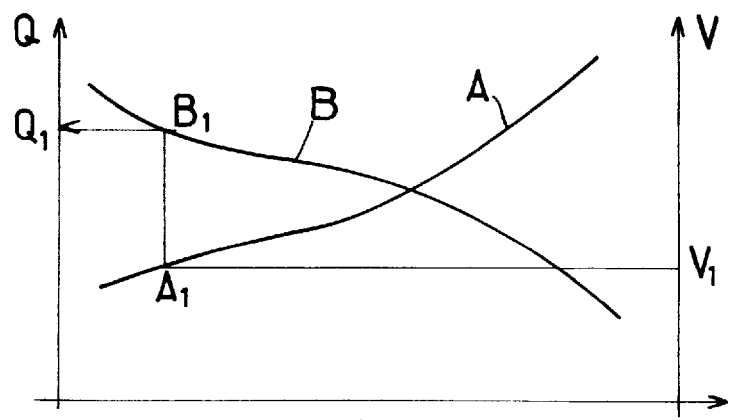
FIG.:3

METHOD AND DEVICE FOR MEASURING THE QUANTITY OF AN ACTIVE PRINCIPLE CONTAINED IN A RESERVOIR

The present invention relates to a method and to a device for measuring the quantity of an active principle contained in a reservoir, as well as to a reservoir designed to allow such a measurement. More particularly, the invention relates to such a method, device and reservoir employed in the context of transdermal delivery of medicinal products assisted by iontophoresis.

FIG. 2 of the attached drawing diagrammatically represents means which can be used for carrying out such delivery. These means essentially comprise, in a known manner, a reservoir 1 comprising a layer 2 of a material, such as a hydratable polymer or "hydrogel", impregnated with a solution of the active principle, this layer 2 being designed to be placed in contact with the skin 3 of a patient. The active principle is present in the solution in an ionized form, so that its passage through the skin of the patient can be assisted by iontophoresis. In order to do this, the reservoir is connected to an electronic module 4 comprising means 5 for generating and means 6 for controlling a so-called "therapeutic" current which passes through the patient between an electrode 7, which may form part of the reservoir 1, and an adjacent electrode 8, so as to establish current lines 9 under the skin of the patient. The ions of the active principle flow down these current lines, starting from the reservoir 1 then crossing the dermis and passing into the underlying capillary vessels. The control means 6, for example a microcontroller, control the amplitude and the waveform of the applied current so that the quantity of active principle passing into the blood is modulated in time according to a precise delivery program, established on the basis of pharmacological considerations.

This program should thus respect the minimum and maximum values of the doses of active principle applied per unit time. An overdose may be highly dangerous for the safety of the patient, whereas an insufficient dose does not allow the desired pharmacological activity to be ensured. It should be pointed out, in this regard, that the quantities of active principle to be delivered do, of course, vary from one active principle to another, and that the delivery program should be capable of adapting to the variations in the permeability of the skin, from one patient to another.

It will be understood that, in order to ensure that the program is followed, it is then necessary for the control means to be fed back with a measurement of the quantity of active principle actually delivered to the patient, all along the delivery time of said active principle.

For this purpose, a method and an apparatus for dosage of the quantities of active principle delivered, operating by integration over time of the "therapeutic" current passing through the patient between the electrode 7 and the electrode 8 are proposed in European Patent Application No. 0,277,314 in the name of R. TAPPER. This method is burdened with the drawback that the current passing between the two electrodes is not necessarily representative of the number of ions of the active principle which have left the reservoir and passed into the blood of the patient. Iontophoresis does in fact have an efficiency which is less than one, and in addition, can vary from one patient to another, and from one condition of the skin of the patient to another, this condition varying progressively during the delivery of the medicinal product, which may commonly last several hours.

Another solution which is theoretically envisageable, but difficult, might consist in in vivo dosage of the quantity of active principle present in the blood of the patient.

The object of the present invention is to provide a method and a device for measuring the quantity of an active principle contained in a reservoir, which does not have the abovementioned drawbacks of the prior art.

A further object of the invention is to provide an active principle reservoir which is suitable for implementing the method according to the invention.

The objects of the invention, as well as others which will emerge on reading the following description, are achieved with a method for measuring the quantity of an active principle contained in an ionized form in a reservoir consisting of a layer of a material impregnated with a solution of this active principle, which is noteworthy in that the conductivity of the impregnated material is measured and a measurement of the quantity of active principle contained in the reservoir is derived from this conductivity measurement. As will be seen hereinbelow, the conductivity or the conductance of the reservoir is a function of the quantity of active principle contained in this reservoir. By subtraction, the quantity of active principle which has passed into the blood of a patient during transdermal delivery of medicinal products can be deduced therefrom.

According to a characteristic of the method according to the invention, in order to measure the conductivity of the impregnated material, a current of predetermined strength is passed through the latter, and the electric voltage which then appears between two electrodes separated by at least a part of the layer of the impregnated material is measured.

In order to implement this method, the invention provides a device comprising a) first and second electrodes placed on either side of and in electrical contact with at least a part of the layer of the impregnated material of the reservoir, b) means for passing the electric current of predetermined strength through the impregnated material and c) means sensitive to the voltage picked up between the electrodes in order to calculate the quantity of active principle contained in the reservoir.

The invention furthermore provides a reservoir which can be used in such a device, comprising a layer of a material which can be impregnated with a solution of the active principle with a view to transdermal delivery of this active principle to a patient, through a face of this layer which is applied against the skin of the patient, noteworthy in that it comprises an electrode permeable to the solution of active principle, applied to the said face of the layer of the impregnatable material.

Other characteristics and advantages of the present invention will emerge on reading the following description and on examining the attached drawing, in which:

FIG. 1 is a diagrammatic representation of a reservoir according to the present invention, in exploded cross-section, FIG. 2 is a diagrammatic representation of a device for implementing the method according to the invention, already partially described in the preamble of the present description, and FIG. 3 is a plot used in the measurement method according to the invention.

Reference is now made to FIG. 1 which shows that the reservoir 1 according to the invention comprises, in addition to the layer 2 of hydrogel impregnated with a solution of active principle in ionized form and the first electrode 7 which applies the therapeutic current, a second electrode 10, for measurement, mounted for example on a frame 10' and placed on that face of the layer 2 which is opposite the face laid against the first electrode 7. Advantageously, the reservoir 1 comprises another layer 12 of neutral hydrogel deposited on the electrode 10 so as to come into contact with the skin of a patient during transdermal delivery of medicinal products assisted by iontophoresis, for purposes which will be described below.

It will be noted, incidentally, that the first electrode 7 may, as a variant, be integral with the electronic module 4, the hydrogel layer 2 of the reservoir being placed in contact with this electrode just before delivery of a medicinal product, for example.

According to the invention, the measurement electrode 10 is permeable to the solution of active principle, so that this solution can wet the skin of the patient. Purely by way of example, this electrode may consist of a fine wire grid, with a mesh spacing of 1 wire /2 mm or 0.5 wire/2 mm, for example.

Furthermore, the device represented in FIG. 2 comprises means 11 supplied by the potential difference picked up between the electrodes 7 and 10 during passage of the therapeutic current established by the generator 5, these means 11 delivering to the microcontroller a voltage signal V which is an image of the said potential difference. This signal is subjected in the microcontroller 6 to an analog/digital conversion with a view to subsequent calculations. The means 11 constitute a matching stage, which matching can be carried out conventionally using a differential amplifier, for example.

As seen hereinabove, the microcontroller 6 controls the amplitude, the wave form, etc. of the current delivered by the generator 5. Thus, the microcontroller knows exactly, the instant when it picks up the voltage V, the current I which passes through the electrode 7 and the layer of hydrogel impregnated with active principle.

From these two parameters, it is possible to deduce the overall conductivity of the layer (2) of hydrogel, which conductivity is a function of the quantity of ions of the active principle which are present in the layer 2 at the moment of the measurement of I and V. If the only ions present in the layer of hydrogel are those of the active principle, the quantity of active principle present in the layer can be deduced from the measurement of the conductivity of the layer alone.

In fact, however, the layer of hydrogen often contains other ionized species. This is, in particular, true when, as is conventional, the active principle is introduced into the layer of hydrogel by means of a saline solution of sodium chloride, for example. If the active principle is present in the solution in the form of positively charged ions, it is clear that the co-ions $Na^+$ of the solution influence, as a function of their concentration and their mobility, the overall conductivity of the layer 2. Similarly, if the electrode 7 is made of silver/silver chloride, $Ag^+$ ions may be found in the layer 2, which affect its conductivity.

In practice, according to the invention, account is taken of all the ions which may affect the conductivity of the layer 2, other than those of the active principle, by carrying out prior calibration operations based on measurements carried out in vitro and/or in vivo, these operations making it possible to establish the plot illustrated by FIG. 3, which makes it possible to derive the quantity of active principle contained in the layer 2 just by measuring the voltage V between the electrodes 7 and 10.

The basis for construction of this plot may be an "in vitro" measurement cell comprising a chamber for a medium holding the ions of an active principle which have passed through a skin sample attached to the reservoir in FIG. 2, under iontophoretic assistance. The concentration of active principle in the holding medium is then periodically determined and the voltage V then observed between the electrodes 7 and 10 is picked up (graph A). By subtraction, graph B, illustrating the decrease in the quantity Q of active principle remaining in the reservoir, as a function of time, is derived from the concentration measurements.

This plot, once set up, is used as follows: during transdermal delivery of a given active principle in a given solution of given starting concentration, a voltage $V_1$ between the electrodes 7 and 10 is measured at some instant. This voltage makes it possible to determine, on the graph A, a point $A_1$ of ordinate $V_1$, and then a point $B_1$ on the graph B, having the abscissa of $A_1$. The ordinate $Q_1$ of $B_1$ gives the quantity of active principle contained at the instant of the measurement in the reservoir according to the invention.

Measurements of concentration in the plasma, carried out in vivo on a patient under treatment by known means, for example chromatographical or electrochemical, might also make it possible to establish the plot in FIG. 3.

According to another advantageous characteristic of the device according to the invention, the microcontroller 6 comprises memory means (not shown) loaded with a table, derived from the plot in FIG. 3, forming a correspondence between a set of values of the voltage V and a set of values of the quantity Q of active principle contained in the reservoir. By virtue of knowledge of this quantity Q at any instant, the microcontroller constructs a feedback signal which can be used in control of the therapeutic current by the microcontroller 6, in order to compel the strength of this current to follow a predetermined time program, corresponding to a predetermined program for medicinal product delivery.

It will be noted that the control of this current thus established makes it possible to take account of variations in the iontophoretic efficiency, from one patient to another, and variations over time of the permeability to the active principle of the skin of a patient.

Of course, the invention is not limited to the embodiment described and represented, which was given only by way of example. Thus, in the period of measuring the quantity of active principle which is passed into the blood of the patient, use may be made of a current having a strength which is different from that of the therapeutic current. The measurement can then be carried out in a current/voltage range which is chosen so as to shield the measurement from possible physiologically induced interference.

Similarly, the reservoir may comprise a measurement electrode 10 having a form other than that of a metal grid, for example that of an open worked film plated with a metal layer, or else an open worked film made of an electrically conducting polymer material.

The layer of hydrogel 12 which covers the external face of the measurement electrode 10 has several functions. First, it is used for ensuring adhesion of the measurement electrode onto the skin of a patient whilst reducing the irritation of the skin. It is also used for isolating the electrode 10 from ions such as $K^+$, $Na^+$, $Cl^-$ normally present on the skin of the patient owing to perspiration. It is also used for protecting the measurement electrode when the reservoir is not applied to the skin of a patient.

The hydratable polymer or hydrogel constituting the layer 2 may be replaced by other materials such as a felt, a sponge or any other material capable of absorbing a liquid.

It is also clear that the invention extends to determination of the quantity of active principle in ionized form which is passed into the blood of a patient by transdermal delivery even though this delivery might not be assisted by iontophoresis. However, it is particularly well suited to an iontophoretic device by virtue of the presence therein of the essential part of the electrical and electronic means necessary.

We claim:

1. Method for measuring the quantity of an active principle contained in an ionized form in a reservoir comprising of a layer of a material impregnated with a solution of said active principle, wherein the conductivity of the impregnated material is measured and a measurement of the quantity of active principle contained in the reservoir is derived from said conductivity measurement.

2. Method according to claim 1, wherein, in order to measure the conductivity of the impregnated material, a current of predetermined strength is passed through the latter, and the electric voltage which then appears between two electrodes separated by at least a part of the layer of the impregnated material is measured.

3. Method according to claim 2, wherein the quantity of active principle contained in the reservoir is derived from a plot established during a prior calibration phase and giving said quantity as a function of said measured voltage.

4. Method according to claim 3, wherein the said plot is established on the basis of measurements of quantities of active principle which have passed through a skin sample under transdermal delivery of the active principle assisted by iontophoresis, carried out in an in vitro measurement cell.

5. Method according to claim 3, wherein the said plot is established on the basis of measurements of quantities of active principle which have passed through the skin of a patient.

6. Device for implementing the method according to claim 1, comprising a) first and second electrodes placed on either side of and in electrical contact with at least a part of the layer of the impregnated material of the reservoir, b) means for passing the electric current of predetermined strength through the impregnated material and c) means sensitive to the voltage picked up between said electrodes in order to calculate the quantity of active principle contained in said reservoir.

7. Device according to claim 6, wherein said calculation means are incorporated in an electronic module for generating and controlling a therapeutic electric current for transdermal delivery of the active principle, assisted by iontophoresis.

8. Device according to claim 7, wherein said means for passing the electric current through the impregnated material comprise a generator delivering a current passing between said first electrode and said second electrode, the latter being in electrical contact with the skin of a patient.

9. Device according to claim 6, wherein the calculation means comprise memory means loaded with a table giving the quantity of active principle contained in the reservoir as a function of the electric voltage measured between the electrodes, the table constituting an image of a plot established during a prior calibration phase and giving said quantity as a function of said measured voltage.

10. Device according to claim 9, comprising means for regulating a therapeutic current on the basis of the measured quantity of active principle, so as to servo the quantity of active principle delivered to a patient to a predetermined time program.

11. Reservoir for implementing the method according to claim 1, comprising a layer of material impregnated with a solution of the active principle for transdermal delivery of said active principle to a patient through a surface of said layer which is applied against the skin of the patient, and a measurement electrode permeable to the solution of active principle, applied to said surface of the layer of impregnated material.

12. Reservoir according to claim 11, wherein said measurement electrode is in the form of a conductive grid.

13. Reservoir according to claim 12, wherein the measurement electrode is covered, on the side which is not in contact with the layer of the impregnated material, with a layer of a neutral hydrogel.

14. Reservoir according to claim 11, wherein the reservoir further comprises an electrode, arranged in electrical contact with a surface of the layer of impregnated material which is opposite the surface in contact with the measurement electrode.

* * * * *